(12) United States Patent
Vom Berg et al.

(10) Patent No.: US 6,537,277 B2
(45) Date of Patent: Mar. 25, 2003

(54) IMPLANT FOR FIXING A BONE PLATE

(75) Inventors: Ingo Vom Berg, Trossingen (DE); Ulrich Fink, Tuttlingen (DE); Manfred Fischer, Tuttlingen (DE); Theodor Lutze, Balgheim (DE); Dieter Weisshaupt, Immendingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 39 days.

(21) Appl. No.: 09/923,282

(22) Filed: Aug. 6, 2001

(65) Prior Publication Data

US 2002/0022844 A1 Feb. 21, 2002

Related U.S. Application Data

(63) Continuation of application No. PCT/EP00/01261, filed on Feb. 16, 2000.

(30) Foreign Application Priority Data

Feb. 20, 1999 (DE) .......................................... 199 07 354

(51) Int. Cl.⁷ ............................................... A61B 17/56
(52) U.S. Cl. ............................. 606/71; 606/69; 606/75
(58) Field of Search .......................... 606/71, 72, 213, 606/70, 69, 151, 61, 75, 104, 86

(56) References Cited

U.S. PATENT DOCUMENTS 2,576,649 A    11/1951  Slind
5,246,443 A  *  9/1993  Mai .............................. 606/78
5,662,655 A  *  9/1997  Laboureau et al. ........... 606/75
6,190,389 B1 *  2/2001  Wellisz et al. ................ 606/69
6,197,037 B1 *  3/2001  Hair ............................ 606/151
6,302,884 B1 * 10/2001  Wellisz et al. ................ 606/69

FOREIGN PATENT DOCUMENTS

| DE | 196 34 697 | 4/1998 |
| DE | 196 34 699 | 4/1998 |
| DE | 299 03 131 | 5/1999 |
| EP | 0 920 837  | 6/1999 |
| WO | 97/29708   | 8/1997 |

\* cited by examiner

Primary Examiner—Pedro Philogene
(74) Attorney, Agent, or Firm—Barry R. Lipsitz

(57) ABSTRACT

To design as simply as possible an implant for fixing a bone plate in an opening of a bone plate and to avoid use of a complicated applicator, it is proposed that the implant be designed as a U-shaped clip, with a bridge and two contact arms protruding transversely from the bridge, the contact arms being capable of receiving a bone plate between them and thereby fixing the clip on the bone plate with the contact arms lying against the upper side and the lower side, respectively, of the bone plate, and with at least one projection on the outer side of the bridge facing away from the contact arms for fixing the clip on the other bone plate, so that a displacement of the clip relative to the other bone plate in the longitudinal direction of the bridge is prevented in at least one direction.

27 Claims, 2 Drawing Sheets

IMPLANT FOR FIXING A BONE PLATE

This application is a continuation of international application number PCT/EP00/01261 filed on Feb. 16, 2000.

BACKGROUND OF THE INVENTION

The invention relates to an implant for fixing a bone plate in an opening of a bone plate.

During the performance of cranial operations access is gained by plate-shaped bone sections being sawed out of the skull bone. After completion of the operation, these have to be fixed in the opening made in the vault of the skull in order that they can become incorporated again in the old position. Implants consisting of several individual parts are known for fixing these bone plates in the opening of the vault of the skull. The individual parts are placed from the upper side and the lower side on the vault of the skull and on the inserted bone plate and thereby fix the bone plate in the vault of the skull. Although these known implants are very user-friendly and have proven their worth in practice, it is necessary to use multipart implants and to insert these with the aid of relatively complicated applicators.

The object of the invention is to create a generic implant which is of simpler construction than known implants and is usable without any special applicators.

SUMMARY OF THE INVENTION

This object is accomplished with an implant of the kind described at the outset, in accordance with the invention, in that it is designed as a U-shaped clip, with a bridge and two contact arms protruding transversely from the bridge, the contact arms being capable of receiving a bone plate between them and thereby fixing the clip on the bone plate with the contact arms lying against the upper side and the lower side, respectively, of the bone plate, and with at least one projection on the outer side of the bridge facing away from the contact arms for fixing the clip on the other bone plate so that a displacement of the clip relative to the other bone plate in the longitudinal direction of the bridge is prevented in at least one direction.

Owing to the above-described construction, it is possible to push several such implants designed as U-shaped clips onto a bone plate in such a way that the clips are held on the bone plate and that the bridge of the clips lies in front of the edge of the bone plate. A bone plate provided, for example, with three such clips can then be inserted into an opening in the vault of the skull in such a way that the projections on the clips prevent the bone plate from entering too far into the opening in the skull. The projections on the outer side of the clip thus determine the position of the bone plate with respect to the surface of the opening in the skull, and this is adequate for fixing the bone plate for the incorporating and healing process. Aside from that, the bone plate placed in the opening of the skull is positioned in the skull opening such that a mark on the inserted plate and a mark on the opening in the skull are in alignment with each other so that the bone plate is also positioned in the circumferential direction in the way in which it was originally arranged in the skull opening. These marks can, for example, be formed by the two halves of a trepanation opening made in the vault of the skull as preparation for the cutting-out of the bone plate.

The clips are preferably fixed on the bone section closing the opening in the vault of the skull. In principle, it is, however, also possible to fix the clips on the vault of the skull and to then place the bone section closing the opening in the opening. The projections on the clips held on the vault of the skull would then also prevent the bone section from sinking in too deeply, and the bone section would thereby be fixed in the opening in the skull.

The new implant is explained herein in conjunction with the positioning of a bone plate in an opening in the skull. It will, however, be understood that this implant will always be usable where a bone plate is to be positioned in an opening of another bone plate.

If the implants have only one projection on the outer side of the bridge, the bone plates will normally only be fixable in one direction relative to each other with such implants. Thus, a bone plate can only be prevented from sinking too deeply into the opening of the other bone plate. A fixing on both sides, on the other hand, is only possible when, in accordance with a preferred embodiment, several projections are provided to center the other bone plate relative to the clip in the longitudinal direction of the bridge. The cooperation of several projections thus makes it possible to prevent displacement of the implant relative to the other bone plate in both directions and to thereby achieve a definite positioning of the two bone plates relative to each other.

Provision is made in a preferred embodiment for the bridge to have on its outer side at an end thereof a projection whose bearing surface on the other bone plate lies substantially in one plane with the bearing surface of the contact arm protruding from the bridge at this end thereof. The two bone plates to be fixed relative to each other can thereby be positioned in one plane. For example, the outer sides are aligned with each other in such a way that the bone plate inserted in an opening in the skull is in precise alignment with the outer side of the skull.

It is particularly advantageous for at least some of the projections on the outer side of the bridge and/or the bridge itself to be capable of elastic displacement or deformation such that the projections protrude less far from the edge of the bone plate on which the clip is held.

Insertion of the bone plate on which the clips are held thus results in a deformation of the bridges and/or the projections, so that after insertion the two bone plates are fixed relative to each other by the elastic force of these projections. These fixing forces can be pure clamping forces which are produced by the elastic deformation of the bridge and/or the projections. It can, however, also be a positive locking, namely when the projections undergo deformation when being inserted and after reaching the end position return to a less deformed initial position again in which the projections lie on both sides against the other bone plate. A combination of frictional engagement and positive locking is, of course, also possible.

Provision is made in a particularly preferred embodiment for the bridge to be of arcuate design in the longitudinal direction with a concave outer side and to be capable of elastic deformation into a more stretched position. Thus, the bridge of the clip positions itself in the central area thereof against the bone plate on which the clip is held, but in the end areas thereof against the other bone plate, which, after the positioning of the bone plates, results in a definite centering and fixing of the bone plates relative to each other.

It is expedient for the bridge to pass at least at one end thereof into the adjacent contact arm via a bend protruding outwardly relative to the bridge and forming a projection for fixing the clip on the other bone plate. Thus such a bend itself also forms a projection, so that it is not necessary to arrange additional parts on the outer side of the bridge. An elastic deformation of this projection is also possible by an arcuate design of the bridge itself, but also by an elastic compression of the bend.

Provision can be made for a projection to be formed on one side of the bridge by a projecting lug protruding transversely from the bridge. In this case, a lug is integrally formed on the outer side of the bridge, for example, by welding, so that it protrudes transversely from the bridge and forms a stop or a bearing surface for the other bone plate.

It is particularly advantageous for a projection to be formed on one side of the bridge by a bend, and for a further projection to be formed on the other side by such a projecting lug.

In particular, the projecting lug can have perforations for receiving bone screws so that after insertion of the bone plates, the projecting lug can be fixed on the other bone plate via bone screws, and an additional and permanent fixing of the two bone plates relative to each other is thereby achieved.

Furthermore, in accordance with a further preferred embodiment, such perforations for receiving bone screws can also be arranged in the contact arms, so that the clips can thereby be additionally fixed on the bone plate on which they are held by the contact arms.

It is also expedient for several projections to be arranged on the outer side of the bridge in the central area thereof and to be distributed over the length thereof. In particular, these projections can serve to establish a frictional engagement between the clip, on the one hand, and the other bone plate, on the other hand, and, in addition, the centering of the two bone plates relative to each other is thereby furthered.

In particular, these projections can be designed so as to be of sawtooth-shaped cross section so that the inserted bone plate is easily inserted, but not readily removable again.

It is also possible for the distance of the projections from the bone plate on which the contact arms fix the clip to be increasingly larger from one end of the bridge to the other. This also aids the centering of the bone plates relative to each other and facilitates the insertion with the formation of clamping forces which increase with the insertion depth.

The contact arms are preferably able to swivel apart in a resilient manner, so that the contact arms normally lie resiliently against the upper side and the lower side, respectively, of the bone plate, and thereby reliably fix the clip on the bone plate.

It is expedient for the contact arms to have at their free end projections which are directed towards each other so that certain differences in the thickness of the bone plates can thereby be compensated.

In particular, the projections can be formed by bends in the contact arms.

In accordance with a preferred embodiment, the fixing of the clips on the bone plate is promoted by the projections on the contact arms tapering to a point.

The contact arms can be of one-part construction. Provision is made in a preferred embodiment for each contact arm to be divided by cutouts extending from the free end thereof into at least two single arms arranged adjacent to each other. The clips are thereby also secured against tilting.

The contact arms can have a profile on their inner side facing the bone plate in order to strengthen the contact there between contact arms and bone plates. In particular, the profile can comprise a number of projections of sawtooth-like cross section so that pushing-on of the clips is facilitated but removal is impeded to a considerable extent.

The implant preferably consists of a metal which is well tolerated by the body, for example, of titanium or an implant steel. Provision can, however, also be made for the implant to consist of an absorbable material so that after a certain time the implant is decomposed and absorbed by the body.

BRIEF DESCRIPTION OF THE DRAWINGS

The following description of preferred embodiments of the invention serves in conjunction with the drawings the purpose of further explanation. In the drawings.

DETAILED DESCRIPTION OF THE INVENTION

Figure 1:
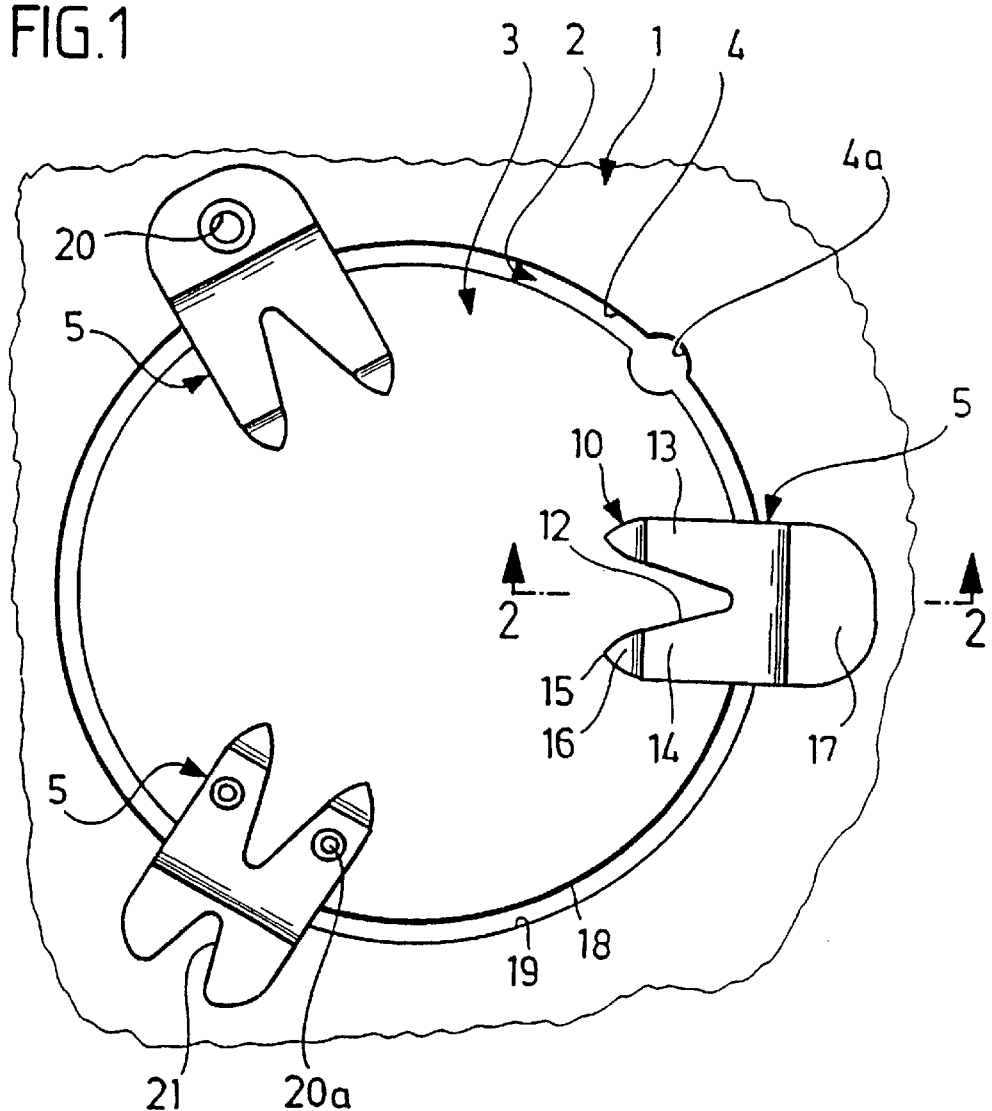
FIG. 1 is a plan view of a circular bone plate after insertion into a circular opening of another bone plate using three clips of different design.

FIG. 1 shows a section of the skull bone 1 from which a circular bone plate 3 has been cut out by a circular incision 2. The bone plate 3 is inserted into this opening 4 again after an operation in order to close the opening 4 created thereby. The circular bone plate 3 is inserted into the opening 4 in such a way that the two halves of a trepanation opening 4a are oriented towards each other. Such a trepanation opening 4a is made in the skull bone 1 before the circular bone plate 3 is cut out of the skull bone 1, and the separating cut of the bone plate 3 is made starting from this trepanation opening 4a.

Figure 2:
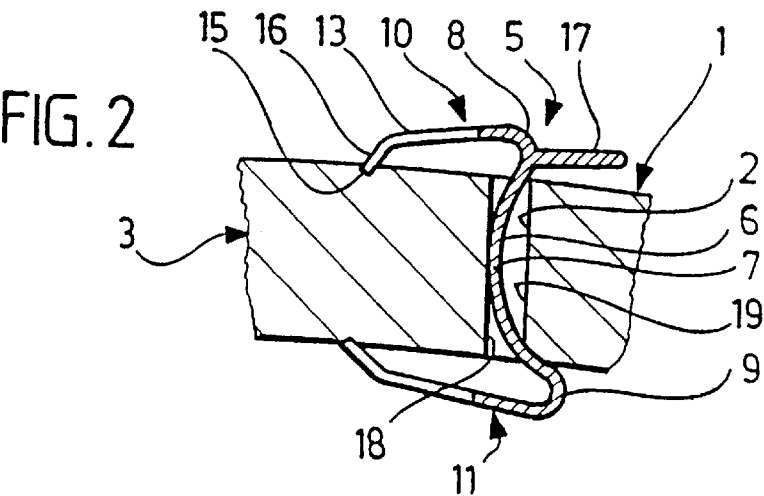
FIG. 2 is a sectional view along line 2—2 in FIG. 1.

Three implants in the form of a U-shaped clip 5 are pushed onto the bone plate 3 from the edge to fix the bone plate 3 in the opening 4. Each clip 5 comprises a bridge 7 which is of arcuate design in the longitudinal direction and hence has a concave outer side 6. At its end, the bridge 7 passes over into contact arms 10 and 11, respectively, via circular arc-shaped bends 8 and 9 (FIG. 2). These contact arms 10 and 11 are each divided by V-shaped cutouts 12 into two single arms 13, 14 arranged adjacent to each other. These single arms 13, 14 terminate at their free end at a point 15 which is arranged at the end of a bend 16, by means of which the single arms 13, 14 are bent at their free end in the direction towards the respective other contact arm.

Into the V-shaped cutout 12 there can be inserted a bone screw via which the contact arms 10 or 11 are pressed against the bone plate 3 so as to achieve an optimum securing of the clip 5 of a bone plate 3. It is also possible to insert such a bone screw through an opening 20a provided in the contact arm 10 or 11, in particular, in the single arms 13, 14.

The clip 5 consists of an elastic material, for example, of a metal such as titanium or implant steel or of an absorbable plastic material, and the contact arms 10, 11 can be swivelled apart against an elastic force.

A projecting lug 17 protruding transversely from the bridge 7 is integrally formed on the outer side 6 of the bridge 7 in the area of the upper bend 8. The projecting lug 17 is of substantially planar design and its lower side is substantially coplanar with the lower side of the upper contact arm 10.

The above-described clip 5 is used to fix the bone plate 3 in the opening 4 of the skull bone 1 in such a way that the healing process can take place. For this purpose, several such clips 5, in the illustrated embodiment three such clips, are pushed from the edge onto the bone plate 3 in offset relation to one another in the circumferential direction, so that the contact arms 10 and 11 lie resiliently on the upper side and the lower side, respectively, of the bone plate 3. Owing to the elastic design of the clips 5, the contact arms 10 and 11 can be bent open to a varying extent which corresponds to the thickness of the bone plate. In any case, they then rest with a spring force on the upper side and on the lower side, respectively, of the bone plate 3, and the tips 15 of the bends 16 enter into contact with the bone plate 3 and thereby fix the clip 5 firmly on the bone plate 3. The fixing is carried out in such a way that the bridge 7 lies with its convex inner side against the edge 18 of the bone plate 3.

The thus prepared bone plate 3 is pushed from the outside into the opening 4 of the skull bone 1. The lower bends 9 of the bridges 7 of the three clips 5 come to rest against the edge 19 of the opening 4, and upon pushing the bone plate 3 further into the opening 4, the bends 9 are displaced in the direction towards the bone plate 3. This results in an elastic deformation of the bridge 7, which is thereby stretched, and the lower contact arm 11 is displaced slightly relative to the bone plate 3. This makes it possible to push the bone plate 3 with the clips 5 placed thereon into the opening 4, although the undeformed lower bends 9 protrude slightly over the contour of the opening 4.

Once the bone plate 3 is fully pressed into the opening 4, the lower bend 9 of the clips 5 on the lower side of the skull bone 1 can move radially outwardly again, i.e., the clip 5 relaxes and the bridge 7 is bent again to a greater extent. The lower bend 9 thereby engages under the skull bone 1 in the area of the edge 19 and centers the clip 5 relative to the skull bone 1, the upper side of the skull bone 1 positions itself against the lower side of the projecting lug 17, the lower side of the skull bone 1 lies against the bend 9, and the dimensions of the clip 5 and the arrangement of the projecting lug 17 and the lower bend 9 are selected such that the skull bone 1 and the bone plate 3 are aligned with each other in the end position (FIG. 2).

In practice, the surgeon can simply press the bone plate 3 provided with the clips 5 into the opening 4. Once the end position is reached, the lower bends 9 snap elastically into the position in which they are pushed out radially, i.e., when pressing in the bone plate 3, the surgeon senses when the end position is reached by the bridges 7 and the bends 9 suddenly relaxing. The bone plate 3 thus locks in the end position. In this end position, the bone plate 3 is then also fixed in both directions relative to the skull bone 1.

An additional fixing is achievable by the projecting lugs 17 being fixed on the skull bone 1 by bone screws. These can, for example, engage through an opening 20 in the projecting lug 17 or be inserted into a V-shaped cutout 21 in the projecting lug 17 (FIG. 1). The three clips 5 shown in FIG. 1 differ from each other by the design in the area of the projecting lugs 17. One projecting lug 17 has an opening 20, a further one has an cutout 21, and the third clip has no such cutouts in the projecting lug 17. Identical or different clips can, of course, be optionally fixed on a bone plate.

Figure 3:
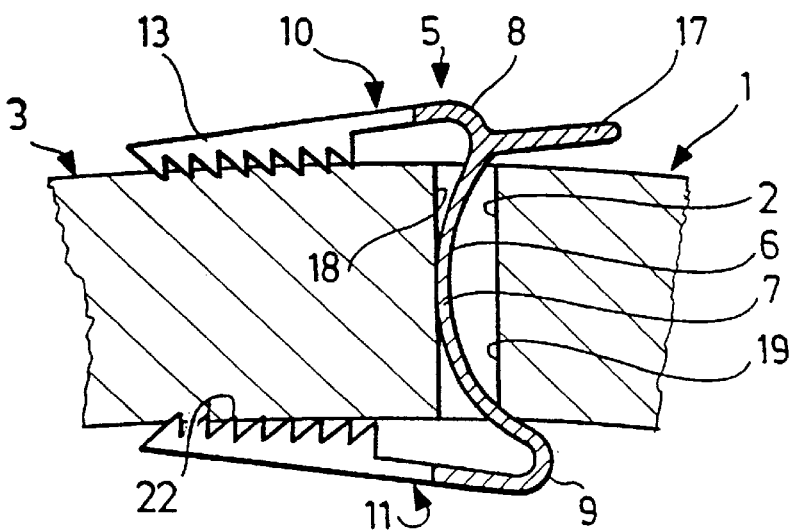
FIG. 3 is a view similar to FIG. 2 in a modified embodiment of a clip.

The embodiment of FIG. 3 corresponds to that of FIG. 2. Like parts therefore bear like reference numerals.

Differently from the embodiment of FIG. 2, the contact arms 10, 11 have no tips 15 or bends 16. Instead, the contact arms 10, 11 have on their inner side facing the bone plate 3 sawtooth-like projections 22 which enable the contact arms 10, 11 to be pushed on easily, but which resist removal of the clip 5.

The embodiment of FIG. 4 is again of similar design to that of FIG. 2. Corresponding parts likewise bear the same reference numerals.

Figure 4:
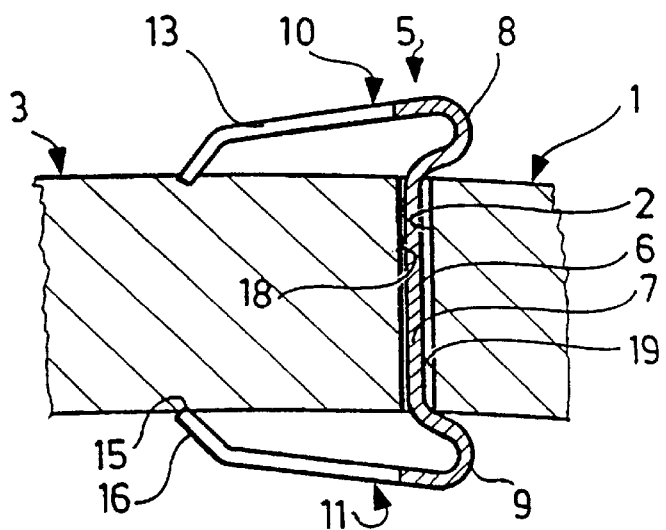
FIG. 4 is a view similar to FIG. 2 in a modified embodiment of a clip.

Differently from the embodiment of FIG. 2, the clip of FIG. 4 has no projecting lug 17. Its stop function is assumed by the upper bend 8. In this clip, the two bends 8 and 9 form projections between which the skull bone 1 is centered relative to the clip 5. To achieve this, provision can be made for the bridge 7 to be of straight-lined design in the area between the bends 8, 9. However, this is not absolutely necessary. Similarly to the way in which it is illustrated in the embodiment of FIG. 2, the bridge could be of bent design.

Figure 5:
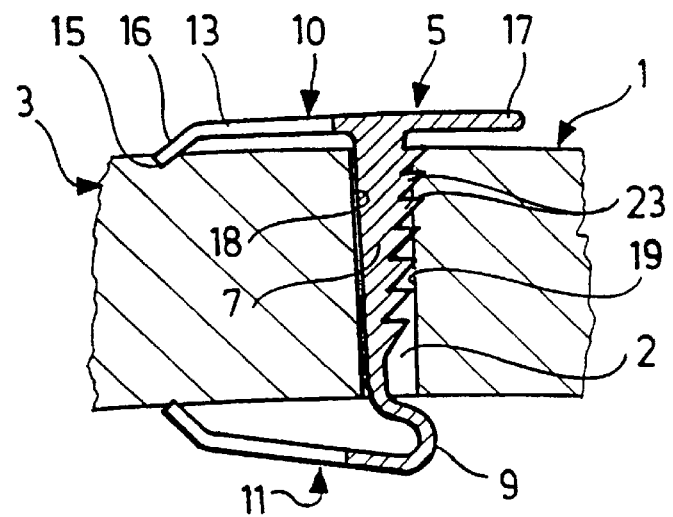
FIG. 5 is a view similar to FIG. 2 in a modified embodiment of a clip.

A similar design of the clip 5 is also provided in the embodiment of FIG. 5. Corresponding parts therefore again bear the same reference numerals as in the embodiment of FIG. 2.

In this embodiment, the upper bend 8 is missing. The upper contact arm 10 of this embodiment passes over directly into the projecting lug 17. The bridge 7 is of straight-lined design and has on its outer side turned away from the bone plate 3 a number of projections 23 of sawtooth-like cross section. The thickness of the bridge 7 increases from the lower bend 9 towards the projecting lug 17.

Insertion of the bone plate 3 with a clip according to FIG. 5 results in a centering of the skull bone 1 between the lower bend 9 and the projecting lug 17. In addition, the projections 23 position themselves to an increasingly strong extent on the skull bone 1 and thus establish a frictional engagement or a clamping connection between bone plate 3 and skull bone 1. A fixing by a combined frictional and positive locking is thereby achieved.

In principle, it is also possible to allow the bridge 7 in the embodiment of FIG. 5 to pass over directly into the lower contact arm 11. In other words, one could dispense with the lower bend 9 forming a centering projection. In this case, the bone plate 3 and the clips 5 would be essentially held in the opening 4 by a clamping connection, with the depth of entry being delimited by the projecting lug 17.

What is claimed is:

1. Implant for fixing a bone plate in an opening of another bone plate, said implant being designed as a U-shaped clip, with a bridge and two contact arms protruding transversely from said bridge, said contact arms holding the clip, which has been positioned on a bone plate, in such a way on said bone plate that the bridge of the clip lies in front of the edge of said bone plate, and with at least one projection on the outer side of the bridge facing away from the contact arms for fixing the clip on the other bone plate, so that a displacement of the clip relative to the other bone plate in the longitudinal direction of the bridge is prevented in at least one direction.

2. Implant in accordance with claim 1, wherein several projections are provided for centering the other bone plate relative to the clip in the longitudinal direction of the bridge.

3. Implant in accordance with claim 1, wherein the bridge has on its outer side at one end thereof a projection whose bearing surface on the other bone plate lies substantially in one plane with the bearing surface of the contact arm protruding from the bridge at this end thereof.

4. Implant in accordance with claim 2, wherein the bridge has on its outer side at one end thereof a projection whose bearing surface on the other bone plate lies substantially in one plane with the bearing surface of the contact arm protruding from the bridge at this end thereof.

5. Implant in accordance with claim 1, wherein at least some of the projections on the outer side of the bridge and/or the bridge itself are capable of elastic displacement or deformation such that the projections protrude less far from the edge of the bone plate on which the clip is held.

6. Implant in accordance with claim 2, wherein at least some of the projections on the outer side of the bridge and/or the bridge itself are capable of elastic displacement or deformation such that the projections protrude less far from the edge of the bone plate on which the clip is held.

7. Implant in accordance with claim 3, wherein at least some of the projections on the outer side of the bridge and/or the bridge itself are capable of elastic displacement or deformation such that the projections protrude less far from the edge of the bone plate on which the clip is held.

8. Implant in accordance with claim 1, wherein the bridge is of arcuate design in the longitudinal direction with a concave outer side and is capable of elastic deformation into a more stretched position.

9. Implant in accordance with claim 1, wherein the bridge passes at least at one end thereof into the respective adjacent contact arm via a bend protruding outwardly relative to the bridge and forming a projection for fixing the clip on the other bone plate.

10. Implant in accordance with claim 9, wherein a projection is formed on one side of the bridge by a bend, and a further projection is formed on the other side thereof by a projecting lug protruding transversely from the bridge.

11. Implant in accordance with claim 10, wherein the projecting lug has openings for receiving bone screws.

12. Implant in accordance with claim 4, wherein the bridge passes at least at one end thereof into the respective adjacent contact arm via a bend protruding outwardly relative to the bridge and forming a projection for fixing the clip on the other bone plate.

13. Implant in accordance with claim 12, wherein a projection is formed on one side of the bridge by a bend, and a further projection is formed on the other side thereof by a projecting lug protruding transversely from the bridge.

14. Implant in accordance with claim 13, wherein the projecting lug has openings for receiving bone screws.

15. Implant in accordance with claim 1, wherein several projections are arranged on the outer side of the bridge in the central area thereof and are distributed over the length thereof.

16. Implant in accordance with claim 15, wherein the projections are designed so as to be of sawtooth-like cross section.

17. Implant in accordance with claim 15, wherein the distance of the projections from the bone plate on which the contact arms fix the clip is increasingly larger from one end of the bridge to the other.

18. Implant in accordance with claim 1, wherein the contact arms are capable of swivelling apart in a resilient manner.

19. Implant in accordance with claim 1, wherein the contact arms have at their free end projections which are directed towards each other.

20. Implant in accordance with claim 19, wherein the projections are formed by bends in the contact arms.

21. Implant in accordance with claim 19, wherein the projections on the contact arms taper to a point.

22. Implant in accordance with claim 1, wherein each contact arm is divided by cutouts extending from the free end thereof into at least two single arms arranged adjacent to each other.

23. Implant in accordance with claim 1, wherein perforations are arranged on one or both of the contact arms for receiving bone screws.

24. Implant in accordance with claim 1, wherein the contact arms have a profile on their inner side facing the bone plate.

25. Implant in accordance with claim 24, wherein the profile comprises a number of projections of sawtooth-like cross section.

26. Implant in accordance with claim 1, wherein said implant consists of a metal which is well tolerated by the body.

27. Implant in accordance with claim 1, wherein said implant consists of an absorbable material.

* * * * *